(12) United States Patent
Takahashi

(10) Patent No.: US 8,794,931 B2
(45) Date of Patent: Aug. 5, 2014

(54) FLUID EJECTION DEVICE AND MEDICAL DEVICE

(75) Inventor: Hideyuki Takahashi, Omachi (JP)

(73) Assignee: Seiko Epson Corporation, Tokyo (JP)

( * ) Notice: Subject to any disclaimer, the term of this patent is extended or adjusted under 35 U.S.C. 154(b) by 272 days.

(21) Appl. No.: 13/332,080

(22) Filed: Dec. 20, 2011

(65) Prior Publication Data

US 2012/0163998 A1   Jun. 28, 2012

(30) Foreign Application Priority Data

Dec. 24, 2010  (JP) ................................. 2010-287188
Jul. 29, 2011   (JP) ................................. 2011-166462

(51) Int. Cl.
| | |
|---|---|
| F04B 49/00 | (2006.01) |
| F04B 49/06 | (2006.01) |
| F04B 17/00 | (2006.01) |
| A61B 17/32 | (2006.01) |
| A61M 1/00  | (2006.01) |

(52) U.S. Cl.
USPC .......... 417/216; 417/44.1; 417/313; 604/152; 606/167

(58) Field of Classification Search
USPC .............. 417/36, 44.1, 45, 313, 413.1, 413.2, 417/415, 2, 216, 244, 253; 606/167; 604/22, 152
See application file for complete search history.

(56) References Cited

U.S. PATENT DOCUMENTS

| | | | | |
|---|---|---|---|---|
| 7,901,374 B2* | 3/2011 | Seto et al. | ........................ | 604/48 |
| 7,955,057 B2* | 6/2011 | Kuehner et al. | ................ | 417/360 |
| 8,251,679 B2* | 8/2012 | Kuehner et al. | ............. | 417/413.1 |
| 8,328,831 B2* | 12/2012 | Pein | ............................... | 606/167 |
| 8,506,584 B2* | 8/2013 | Seto et al. | ....................... | 606/167 |
| 2010/0049228 A1 | 2/2010 | Kuehner et al. | | |
| 2010/0082053 A1* | 4/2010 | Hama et al. | .................... | 606/167 |
| 2010/0111708 A1* | 5/2010 | Seto et al. | ..................... | 417/44.1 |
| 2011/0054505 A1* | 3/2011 | Kojima et al. | ................. | 606/167 |
| 2011/0213396 A1* | 9/2011 | Tabata et al. | ................... | 606/167 |

FOREIGN PATENT DOCUMENTS

| | | |
|---|---|---|
| JP | 2010-509542 | 3/2010 |
| WO | 2008058704 | 5/2008 |

* cited by examiner

*Primary Examiner* — Peter J Bertheaud
(74) *Attorney, Agent, or Firm* — Workman Nydegger

(57) ABSTRACT

A fluid ejection device includes: a pulse generation unit that changes the volume of a fluid chamber using a volume changing section to eject pulsating flow; a fluid supply unit including a pump chamber and a pump chamber volume changing section that changes the volume of the pump chamber to supply the fluid to the pulse generation unit; a drive control unit that inputs a pulsating flow drive signal for driving the pump chamber volume changing section and inputs a fluid supply drive signal for driving the fluid supply unit; and an operation command input unit that inputs an operation command to the drive control unit, wherein the fluid supply drive signal and the pulsating flow drive signal are input in conjunction with the input of the operation command.

14 Claims, 7 Drawing Sheets

FLUID EJECTION DEVICE AND MEDICAL DEVICE

BACKGROUND

1. Technical Field

The present invention relates to a fluid ejection device and a medical device including the fluid ejection device.

2. Related Art

In a fluid ejection device such as a water jet knife that excises or incises living tissue using high-pressure fluid, a pump that supplies fluid (for example, physiological saline or Ringer's solution) at stable pressure over a long period of time is required. For example, JP-T-2010-509542 discloses a medical pump employing a technique of supplying fluid without interruption by alternately operating a plurality of pistons (plungers).

However, the above technique of the related art has a problem in that the mechanism for driving the plurality of plungers and the control means thereof are complex. Moreover, there is another problem in that it is difficult to secure high reliability of the pump, simplify the maintenance, and decrease manufacturing costs. On the other hand, a single plunger may be used in order to simplify the structure or the control thereof. However, if a single plunger is used, the size of the pump increases since a large amount of fluid has to be secured in a fluid supply unit, and an amount of fluid sufficient for ejection has to be secured in a pump chamber.

SUMMARY

An advantage of some aspects of the invention is to solve at least a part of the problems described above, and the invention can be implemented as the following forms or application examples.

APPLICATION EXAMPLE 1

This application example of the invention is directed to a fluid ejection device including: a pulse generation unit that changes the volume of a fluid chamber using a volume changing section to eject pulsating flow; a fluid supply unit including a pump chamber and a pump chamber volume changing section that changes the volume of the pump chamber to supply the fluid to the pulse generation unit; a drive control unit that inputs a pulsating flow drive signal for driving the pump chamber volume changing section and inputs a fluid supply drive signal for driving the fluid supply unit; and an operation command input unit that inputs an operation command to the drive control unit, wherein the fluid supply drive signal and the pulsating flow drive signal are input in conjunction with the input of the operation command, wherein the drive control unit drives the pump chamber volume changing section using the fluid supply drive signal so that the volume of the pump chamber increases toward a second volume level when the operation command is not input or when the volume of the pump chamber has reached a first volume level, and the operation command is input, and the volume of the pump chamber decreases toward the first volume level until the volume reaches the first volume level when the operation command is input.

According to this application example, since the supply of fluid to the pulse generation unit and the generation of pulses in the fluid by the pulse generation unit and ejection of the fluid are controlled in conjunction with the input of the operation command, it is possible to start generation of pulsating flow in conjunction with ejection of fluid. Moreover, it is possible to stop ejection of fluid in conjunction with stopping of generation of pulsating flow. When performing surgery with ejection of pulsating flow as in the case of a water jet knife, and a treatment such as excision or incision is stopped, ejection of fluid as well as generation of pulsating flow may often be stopped. Thus, by limiting the amount of ejected fluid to an amount as small as necessary by interlocking the fluid supply drive signal and the pulsating flow drive signal, it is possible to eject a sufficient amount of fluid even when a small amount of fluid is secured in the fluid supply unit. Therefore, it is possible to decrease the size of a fluid ejection device using a single plunger, for example.

Moreover, when the operation command is not input (ejection of fluid is not performed), and the volume of the pump chamber has reached the first volume level, and the operation command is input (the fluid being ejected is exhausted), the volume of the pump chamber moves toward the second volume level. That is, when fluid ejection is not performed, the operation of feeding fluid into the pump chamber starts. Moreover, when the operation command is input (ejection of fluid is performed), the volume of the pump chamber moves toward the first volume level until the volume reaches the first volume level, and fluid ejection is performed. Therefore, since fluid is fed into the pump chamber whenever the ejection stops, fluid is always secured in the pump chamber, and the operator can continue operations without paying any particular attention. As a result, according to the above aspect, even when a small amount of fluid is secured in the pump chamber, a sufficient amount of fluid is ejected, and the size of the fluid ejection device can be decreased.

APPLICATION EXAMPLE 2

This application example of the invention is directed to the fluid ejection device of the above application example, wherein the rate of increase of the volume of the pump chamber in which the fluid is fed into the pump chamber is faster than the rate of decrease of the volume of the pump chamber in which the fluid is delivered from the pump chamber.

According to this configuration, since the rate of increase of the volume of the pump chamber in which the fluid is fed into the pump chamber is faster than the rate of decrease of the volume of the pump chamber in which the fluid is delivered from the pump chamber, fluid is fed into the pump chamber at a high speed when fluid is not ejected. Thus, since fluid is fed into the pump chamber at a high speed whenever ejection stops, fluid is always secured in the pump chamber, and the operator can continue operations without paying any particular attention. As a result, according to this configuration, even when a small amount of fluid is secured in the pump chamber, a sufficient amount of fluid is ejected, and the size of the fluid ejection device can be decreased.

APPLICATION EXAMPLE 3

This application example of the invention is directed to the fluid ejection device of the above application example, wherein the drive control unit inputs the pulsating flow drive signal after a first period elapses after the fluid supply drive signal is input and stops inputting the fluid supply drive signal after a second period elapses after the input of the pulsating flow drive signal stops.

According to this configuration, pulsating flow is generated after a first period elapses after the supply and ejection of fluid are started, and the supply and ejection of fluid are stopped after a second period elapses after generation of the pulsating flow stops. Thus, since pulsating flow can be generated after fluid is stably supplied up to the fluid ejection tube when ejection of pulsating flow is repeatedly started and stopped, an amount of fluid sufficient for generating pulsating flow is secured in the pump chamber. Thus, it is possible to prevent air (or 'nothing') from being ejected rather than fluid. Moreover, when pulsating flow is generated after fluid is stably supplied up to the fluid ejection tube, since bubbles rarely enter into the fluid ejection device, ejection can be performed stably.

APPLICATION EXAMPLE 4

This application example of the invention is directed to the fluid ejection device of the above application example, wherein the fluid supply unit includes a second volume level detection sensor that detects arrival of the volume of the fluid stored in the pump chamber at the second volume level, a first volume level detection sensor that detects arrival of the volume at the first volume level, and a random level detection sensor that detects arrival of the volume at an arbitrary position between the first volume level and the second volume level.

According to this configuration, the arrival of the volume of fluid stored in the fluid supply unit at the maximum volume level or the minimum volume level is preferably detected by a sensor. Moreover, the operator can set a point using the random level detection sensor, at which the operator recognizes that the volume has approached the minimum volume level. Thus, the ejection of fluid will not be stopped suddenly, and an appropriate measure can be taken.

APPLICATION EXAMPLE 5

This application example of the invention is directed to the fluid ejection device of the above application example, wherein the first volume level is a value where the volume of the pump chamber reaches its minimum, and the second volume level is a value where the volume of the pump chamber reaches its maximum.

According to this configuration, when the operation command is not input (ejection of fluid is not performed), the volume of the pump chamber has reached the minimum volume level, and the operation command is input (the fluid being ejected is exhausted), the volume of the pump chamber moves toward the maximum volume level. That is, when fluid ejection is not performed, the operation of feeding fluid into the pump chamber starts. Moreover, when the operation command is input (ejection of fluid is performed), the volume of the pump chamber moves toward the minimum volume level until the volume reaches the minimum volume level, and fluid ejection is performed. Therefore, since fluid is fed into the pump chamber whenever the ejection stops, fluid is always secured in the pump chamber, and the operator can continue operations without paying any particular attention. As a result, according to the above aspect, even when a small amount of fluid is secured in the pump chamber, a sufficient amount of fluid is ejected, and the size of the fluid ejection device can be decreased.

APPLICATION EXAMPLE 6

This application example of the invention is directed to the fluid ejection device according to the above application example, wherein the pump chamber includes a plunger and a cylinder in which the plunger is inserted, and the pump chamber volume changing section is a plunger driving section that moves the plunger within the cylinder.

According to this configuration, a sufficient amount of fluid is ejected even when a small amount of fluid is secured in the cylinder, and surgery can be performed. Thus, it is possible to configure the fluid ejection device with a single plunger fluid supply unit of which the structure and control can be simplified. As a result, it is possible to provide a fluid ejection device in which it is possible to secure high reliability of the pump, simplify the maintenance, and decrease manufacturing costs.

APPLICATION EXAMPLE 7

This application example of the invention is directed to the fluid ejection device of the above application example, wherein the operation command input unit is a switch, a foot switch, or a voice recognition device.

According to this configuration, the operator can output the operation command by closing the switch on the hand or stepping on the foot switch under the foot. Alternatively, the operator can output the operation command by uttering sounds toward a microphone disposed on the head of the operator or in the vicinity thereof. In this way, the operator can operate the fluid ejection device at a desired point in time by concentrating attention on the hand.

APPLICATION EXAMPLE 8

This application example of the invention is directed to a medical device which uses the fluid ejection device of the above aspect.

According to this application example, by using the fluid ejection device as a medical device, it is possible to more effectively provide excellent characteristics as a surgical tool.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, embodiments of the invention will be described with reference to the drawings. In the following respective drawings, constituent elements are depicted to scales different from the actual one for facilitating the reading of the drawings.

Figure 1:
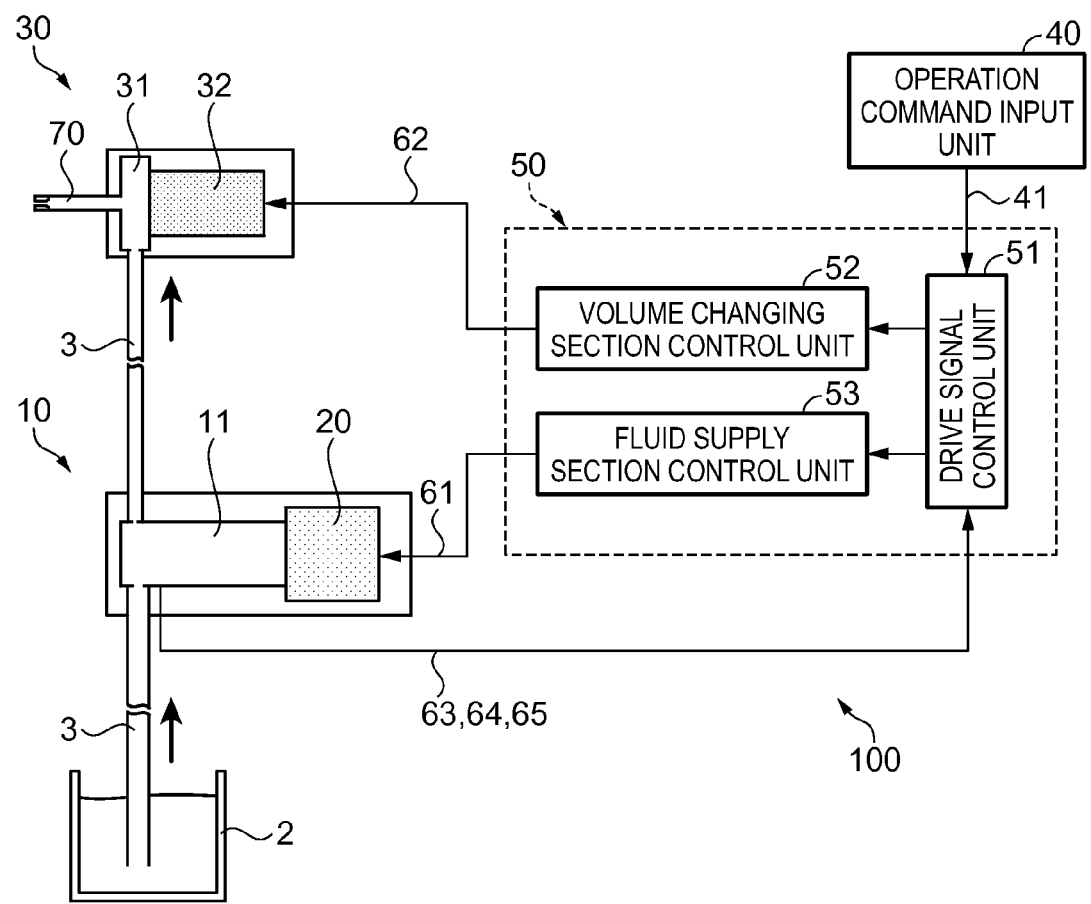
FIG. 1 is a simplified view showing the configuration of a fluid ejection device according to the present embodiment.

FIG. 1 is a simplified view showing the configuration of a fluid ejection device according to the present embodiment. In the present embodiment, although the fluid ejection device is described as being ideal for a medical device, the functions of excising, incising, peeling, fracturing, and the like are not limited to the use in a medical field.

As shown in FIG. 1, a fluid ejection device 100 according to the present embodiment includes a fluid container 2, a fluid supply unit 10, a pulse generation unit 30, an operation command input unit 40, and a drive control unit 50. The fluid container 2 and the fluid supply unit 10 are connected by a connection tube 3, and the fluid supply unit 10 and the pulse generation unit 30 are connected by the connection tube 3. Physiological saline is preferably used as the fluid stored in the fluid container 2.

The fluid supply unit 10 is a single-plunger pump which is an example of the present embodiment, which includes a pump chamber 11, a pump chamber volume changing section 20, and the like.

The pulse generation unit 30 includes a fluid chamber 31, a volume changing section 32, a fluid ejection tube 70, and the like. The fluid ejection device 100 is configured such that the pulse generation unit 30 converts the fluid supplied by the fluid supply unit 10 from the fluid container 2 to the pulse generation unit 30 into pulsating flow, and the pulsating flow is ejected from the fluid ejection tube 70.

The operation command input unit 40 is a signal input means such as a switch that inputs a command from an operator to the drive control unit 50 as an operation command 41, and is provided on the hand of the operator or under the foot of the operator. More specifically, the operation command input unit 40 is preferably any one of a switch, a foot switch, and a voice recognition device. By doing so, the operator can output the operation command 41 by closing the switch on the hand or stepping on the foot switch under the foot. Alternatively, the operator can output the operation command 41 by uttering sounds toward a microphone disposed on the head of the operator or in the vicinity thereof.

The drive control unit 50 includes a drive signal control unit 51, a volume changing section control unit 52, a fluid supply section control unit 53, and the like. The drive signal control unit 51 receives the operation command 41 and causes the volume changing section control unit 52 to input a predetermined pulsating flow drive signal (pulse drive signal 62) to the pulse generation unit 30. Moreover, the drive signal control unit 51 receives the operation command 41 and causes the fluid supply section control unit 53 to input a predetermined fluid supply drive signal (pump drive signal 61) to the fluid supply unit 10.

Figure 2:
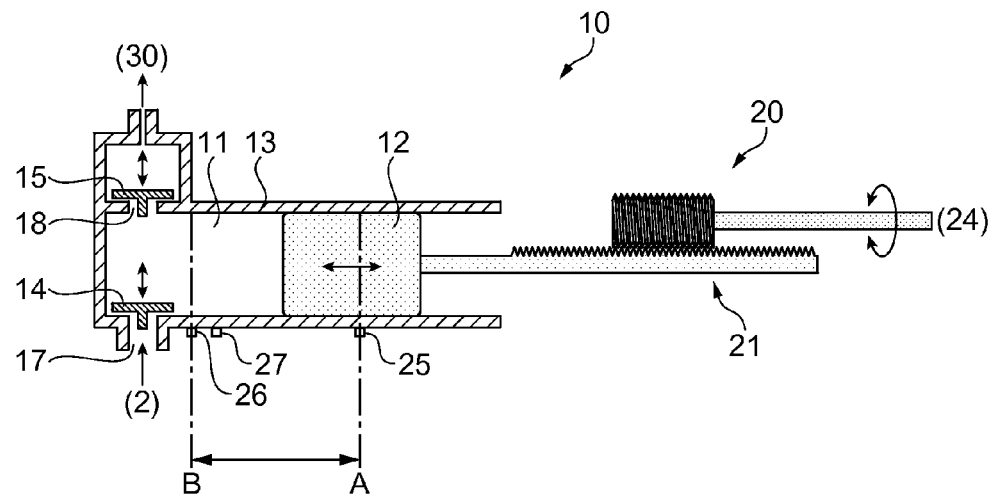
FIG. 2 is a side cross-sectional view showing an exemplary configuration of a fluid supply unit according to the present embodiment.

FIG. 2 is a side cross-sectional view showing an exemplary configuration of the fluid supply unit 10 according to the present embodiment. The fluid supply unit 10 preferably includes a pump chamber 11, a plunger 12, a cylinder 13 in which the plunger 12 is inserted, a pump chamber volume changing section 20, and the like. An inlet port 17 in which fluid is fed from the fluid container 2 and an outlet port 18 from which fluid is delivered to the pulse generation unit 30 are provided in the end portion of the cylinder 13 that forms the pump chamber 11. The inlet port 17 and the outlet port 18 include an inlet valve 14 and an outlet valve 15, respectively.

The pump chamber volume changing section 20 includes a gear structure 21 such as a warm lock and a rotating mechanism 24 (not shown). The pump chamber volume changing section 20 converts a rotational motion of the rotating mechanism 24 which rotates in a forward or reverse direction in accordance with the pump drive signal 61 into a reciprocating motion of the plunger 12.

The pump chamber 11 is formed by an area surrounded by the plunger 12 and the cylinder 13. The pump chamber 11 can change its volume within a range from the maximum volume level (second volume) A where the volume reaches its maximum within a movable range of the plunger 12 to the minimum volume level (first volume) B where the volume reaches its minimum within the movable range. Moreover, on the outer circumference of the cylinder 13, a second volume level detection sensor 25 that detects arrival of the plunger 12 at the maximum volume level A, a first volume level detection sensor 26 that detects arrival of the plunger 12 at the minimum volume level B, and a random level detection sensor 27 that detects a no fluid warning level positioned between the minimum volume level B and the maximum volume level A and a little closer to the maximum volume level A than the minimum volume level B may be provided (the position of the random level detection sensor 27 will be described later). Depending on the movement of the plunger 12, the second volume level detection sensor 25, the first volume level detection sensor 26, and the random level detection sensor 27 output a full fluid signal 63, a no fluid signal 64, and a warning signal 65 to the drive signal control unit 51, respectively (see FIG. 1).

The drive control unit 50 causes the fluid supply section control unit 53 to output the predetermined pump drive signal 61 to the rotating mechanism 24 of the pump chamber volume changing section 20 in accordance with the respective states of the operation command 41, the full fluid signal 63, the no fluid signal 64, and the warning signal 65. The pump drive signal 61 outputs one of the three levels corresponding to forward rotation (+v), no rotation (0), and reverse rotation (−v) to thereby control the rotating mechanism 24.

When the pump drive signal 61 indicates reverse rotation (−v), the rotating mechanism 24 moves the plunger 12 in a direction from the minimum volume level B to the maximum volume level A. When the pump drive signal 61 indicates forward rotation (+v), the rotating mechanism 24 moves the plunger 12 in a direction from the maximum volume level A to the minimum volume level B. Moreover, when the pump drive signal 61 indicates no rotation (0), the rotating mechanism 24 does not move the plunger 12. That is, when the pump drive signal 61 indicates reverse rotation (−v), fluid is fed into the pump chamber 11 (in this case, the inlet valve 14 is opened and the outlet valve 15 is closed in accordance with the movement of the fluid). When the pump drive signal 61 indicates forward rotation (+v), fluid is delivered from the pump chamber 11 (in this case, the inlet valve 14 is closed and the outlet valve 15 is opened in accordance with the movement of the fluid).

Moreover, the fluid supply unit 10 is preferably configured such that the speed of feeding fluid into the pump chamber 11 is about 100 times faster than the speed of delivering fluid from the pump chamber 11. Specifically, a control means (not shown) such as a gear system is employed so that the output of the rotating mechanism 24 has a high rotation speed and a low torque when rotating in a direction of pulling the plunger 12 (in a suctioning direction from the minimum volume level B to the maximum volume level A). Moreover, the output of the rotating mechanism 24 has a low rotation speed and a high torque when rotating in a direction of pushing the plunger 12 (in a delivery direction from the maximum volume level A to the minimum volume level B). Moreover, it is preferable to decrease the length of a flow path from the fluid container 2 to the inlet port 17 and increase the cross-sectional area of the flow path to thereby decrease inertance so that the suctioning can be realized with rotation at a low torque.

Figure 3:
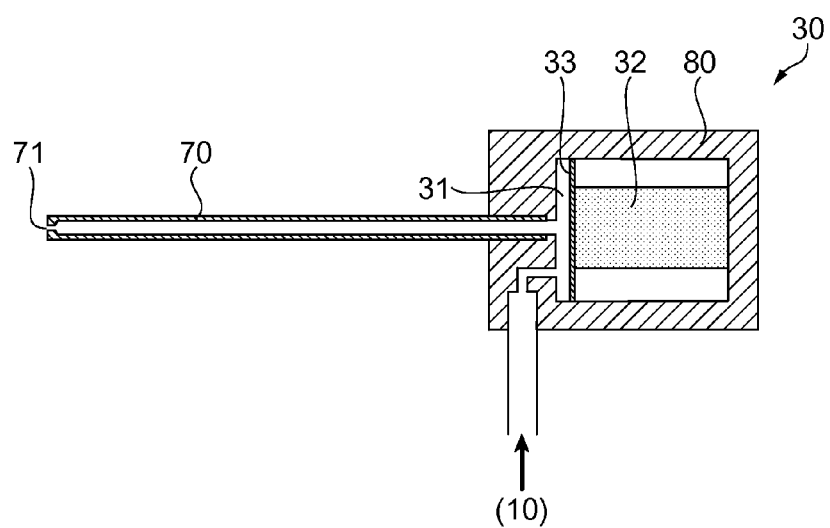
FIG. 3 is a side cross-sectional view showing an exemplary configuration of a pulse generation unit according to the present embodiment.

FIG. 3 is a side cross-sectional view showing an exemplary configuration of the pulse generation unit 30 according to the present embodiment. The pulse generation unit 30 includes the fluid chamber 31, the volume changing section 32, a diaphragm 33, a case 80, the fluid ejection tube 70, and the like.

The fluid chamber 31 is formed by an area surrounded by a part of the case 80 and the diaphragm 33. The volume changing section 32 is connected to the fluid chamber 31 through the diaphragm 33. The volume changing section 32 is expanded and contracted in accordance with the pulse drive signal 62 (see FIG. 1) sent from the volume changing section control unit 52 to the volume changing section 32, whereby the diaphragm 33 is driven to change the volume of the fluid chamber 31 and generate pulsating flow. A piezoelectric element is preferably used as the volume changing section 32.

The fluid ejection tube 70 is connected to the fluid chamber 31 and a nozzle 71 is formed at a distal end of the fluid ejection tube 70. When the fluid chamber 31 is filled with fluid supplied from the fluid supply unit 10, the fluid flows out of the fluid chamber 31 to be ejected from the nozzle 71. When the pulse generation unit 30 is operated, and the volume of the fluid chamber 31 is changed, pulsating flow is ejected.

Figure 4A:
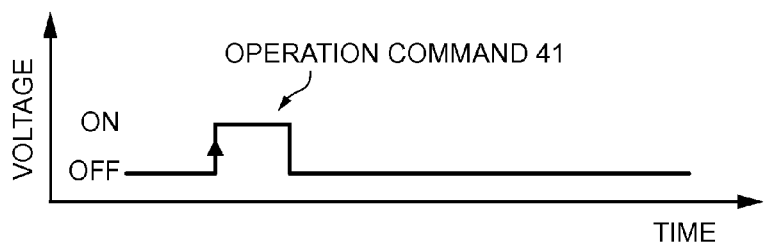
FIGS. 4A to 4C are waveform diagrams showing an operation command and a pulse drive signal according to the present embodiment.
Figure 4B:
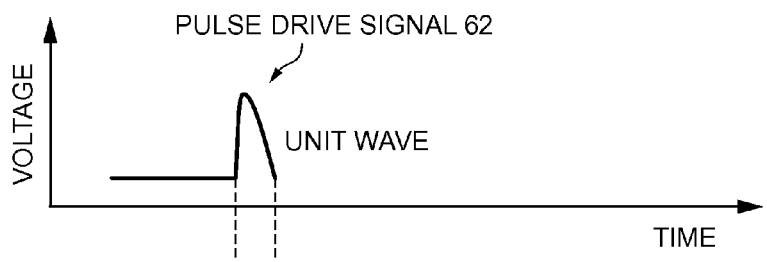
Figure 4C:
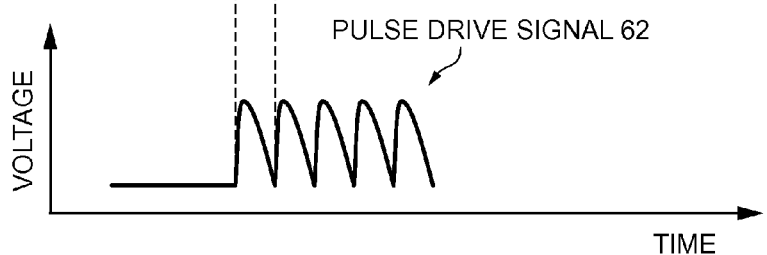

FIGS. 4A to 4C are waveform diagrams showing the operation command 41 and the pulse drive signal 62 according to the present embodiment. When the operation command 41 as shown in FIG. 4A is input, the drive control unit 50 causes the volume changing section control unit 52 to output the pulse drive signal 62 to the volume changing section 32. The pulse drive signal 62 is output as a single shot of unit waves of a voltage waveform as shown in FIG. 4B or as a continuous shot of the unit waves as shown in FIG. 4C in accordance with the control of the drive signal control unit 51. In this way, the volume changing section 32 is expanded and contracted, and pulses are generated in the fluid filled in the fluid chamber 31 by the diaphragm 33.

Figure 5A:
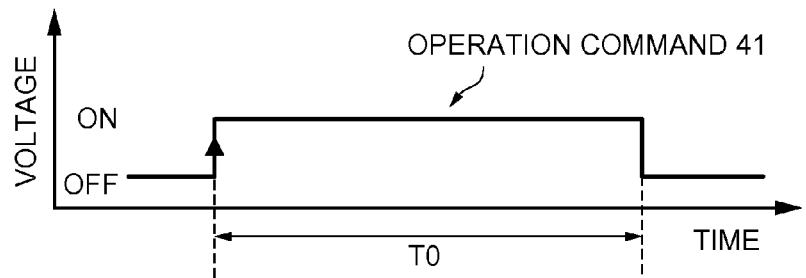
FIGS. 5A to 5D are waveform diagrams showing variations of the pulse drive signal according to the present embodiment.
Figure 5B:
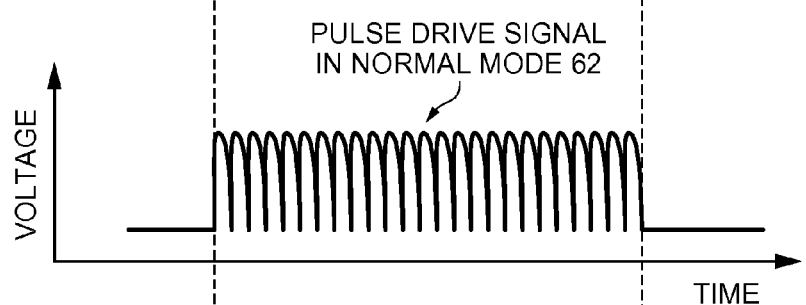
Figure 5C:
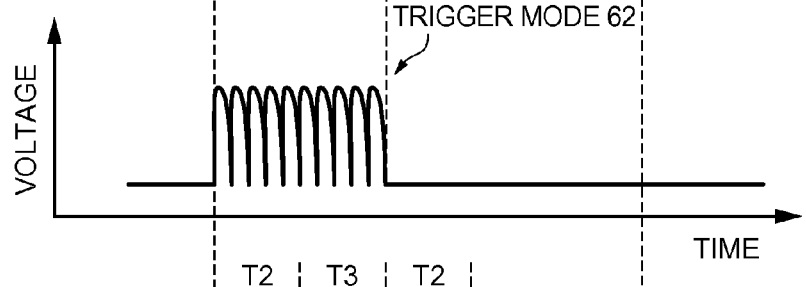
Figure 5D:

FIGS. 5A to 5D are waveform diagrams showing variations of the pulse drive signal 62 according to the present embodiment. FIGS. 5B to 5D show examples of the output waveform of the pulse drive signal 62 when the operation command 41 outputs an ON signal during a period T0 as shown in FIG. 5A. These variations can be selected in accordance with preset control specifications of the drive signal control unit 51.

In FIG. 5B, the pulse drive signal 62 is output continuously during the period T0 (normal mode).

In FIG. 5C, the pulse drive signal 62 is output continuously during a predetermined period T1 from the point in time when the operation command 41 is output regardless of the length of T0 (trigger mode). Therefore, depending on the set period of T1, the pulse drive signal 62 maybe continuously output even when the operation command 41 is in the OFF state, and the pulse drive signal 62 may not be output even when the operation command 41 is in the ON state.

In FIG. 5D, the pulse drive signal 62 that continues for a period T2 is repeated with a break period of T3. The period where the repeated output continues may end at T0 as shown in FIG. 5D (burst mode), and the period may not depend on the length of T0, but although not shown in the drawing, the repeated output may continue for a preset period (trigger burst mode).

Next, the operation of the fluid ejection device 100 having the above configuration will be described.

Figure 6:
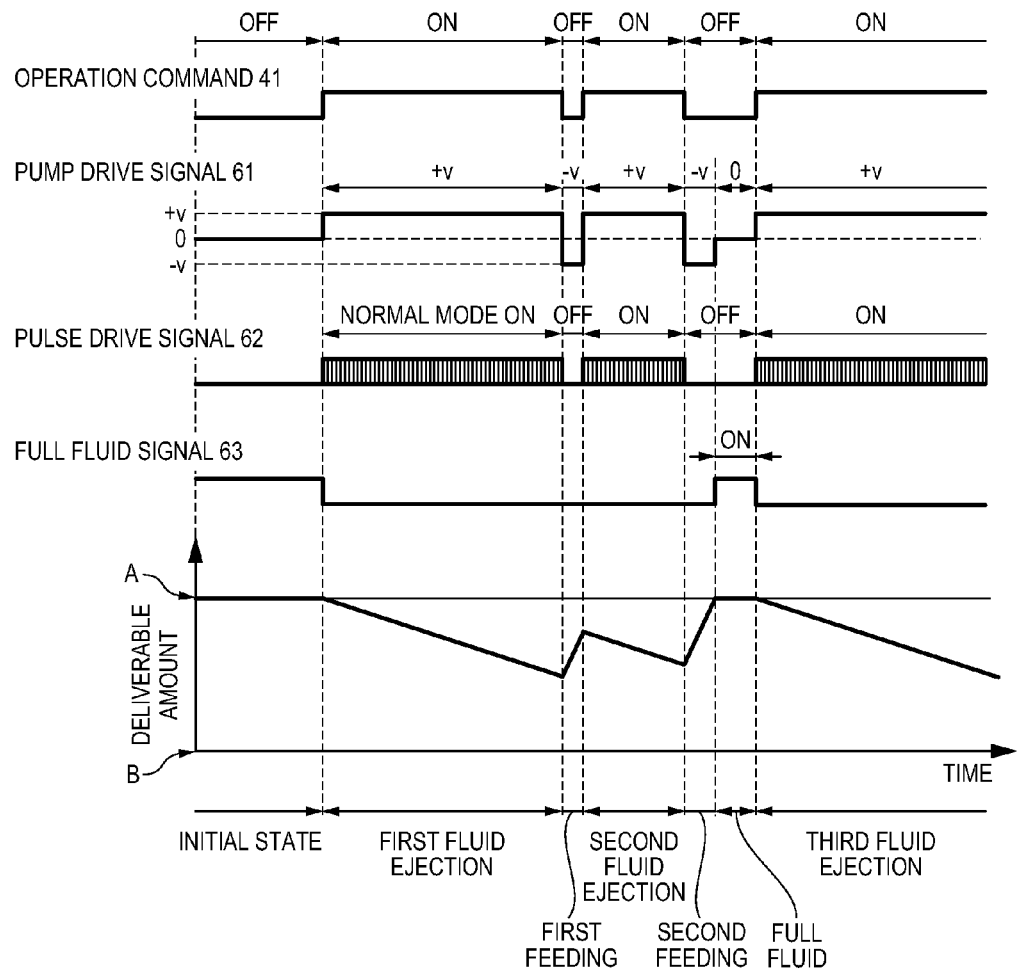
FIG. 6 is a timing diagram showing a basic operation of the fluid supply unit according to the present embodiment.

FIG. 6 is a timing diagram showing a basic operation of the fluid supply unit 10 according to the present embodiment. Specifically, FIG. 6 shows the relationship between the operation command 41, the pump drive signal 61, the pulse drive signal 62, and the amount of fluid that can be delivered from the fluid supply unit 10 (the residual amount of fluid that can be delivered from the pump chamber 11). This example shows the operation of the fluid supply unit 10 when the pulse drive signal 62 is set in the normal mode (FIG. 5B). The operation of the fluid supply unit 10 will be described with reference to FIGS. 1, 2, and 6.

Initial State

First, as the initial state of the fluid ejection device 100, a full fluid state in which fluid is filled in the fluid container 2, the fluid supply unit 10, the pulse generation unit 30, and the connection tube 3 connected thereto, and the plunger 12 is positioned at a position corresponding to the maximum volume level A is created. The operation command 41 and the pulse drive signal 62 are in the OFF state, and the pump drive signal 61 is in the no rotation (0) state.

First Fluid Ejection

Subsequently, when the operator outputs a command to the operation command input unit 40, and the operation command 41 is turned ON, the drive control unit 50 changes the pump drive signal 61 to the forward rotation (+v) state, and outputs the pulse drive signal 62 continuously.

When the pump drive signal 61 is in the forward rotation (+v) state, the plunger 12 starts moving at a predetermined speed in a direction from the maximum volume level A to the minimum volume level B. When the internal pressure of the pump chamber 11 increases, the inlet valve 14 is closed, and the outlet valve 15 is opened, whereby delivery of fluid toward the pulse generation unit 30 starts. The pulse generation unit 30 which is already filled with fluid starts ejecting fluid from the nozzle 71 (see FIG. 3).

At the same time, the volume changing section 32 having received the continuous pulse drive signal 62 is expanded and contracted to cause the diaphragm 33 to generate pulses in the fluid filled in the fluid chamber 31. In this way, the fluid ejected from the nozzle 71 becomes pulsating flow. Moreover, the amount of deliverable fluid gradually decreases with the amount of ejected fluid.

First Feeding

Subsequently, when the operator stops outputting a command, and the operation command 41 is turned OFF, the drive control unit 50 changes the pump drive signal 61 to the reverse rotation (−v) state, and stops outputting the continuous pulse drive signal 62.

When the pump drive signal 61 is in the reverse rotation (−v) state, the plunger 12 starts moving at a predetermined speed in a direction opposite to the previous direction, from the minimum volume level B to the maximum volume level A. When the internal pressure of the pump chamber 11 decreases, the outlet valve 15 is closed, and the inlet valve 14 is opened, whereby suctioning of fluid from the fluid container 2 starts. Since delivery of fluid to the pulse generation unit 30 stops, ejection of fluid from the nozzle 71 stops. The amount of deliverable fluid gradually increases with the amount of suctioned fluid.

At the same time, since the output of the continuous pulse drive signal 62 stops, the expanding and contracting operation of the volume changing section 32 stops, and the change in volume of the fluid chamber 31 also stops.

Second Fluid Ejection and Second Feeding

When the plunger 12 is positioned at a position between the maximum volume level A and the minimum volume level B, the above operation can be repeated continuously in accordance with the command from the operator.

Full Fluid

When the operation command 41 is continuously in the OFF state with no command output from the operator, the plunger 12 finally reaches the maximum volume level A. The second volume level detection sensor 25 detects arrival of the plunger 12 at the maximum volume level A and outputs the full fluid signal 63 to the drive signal control unit 51. Upon receiving the full fluid signal 63, the drive signal control unit 51 changes the pump drive signal 61 to the no rotation (0) state, and the plunger 12 stops its movement.

Subsequently, the operation of the fluid supply unit 10 when the operator continuously outputs a command to the operation command input unit 40, namely ejection is continued for a long period of time, will be described.

Figure 7:
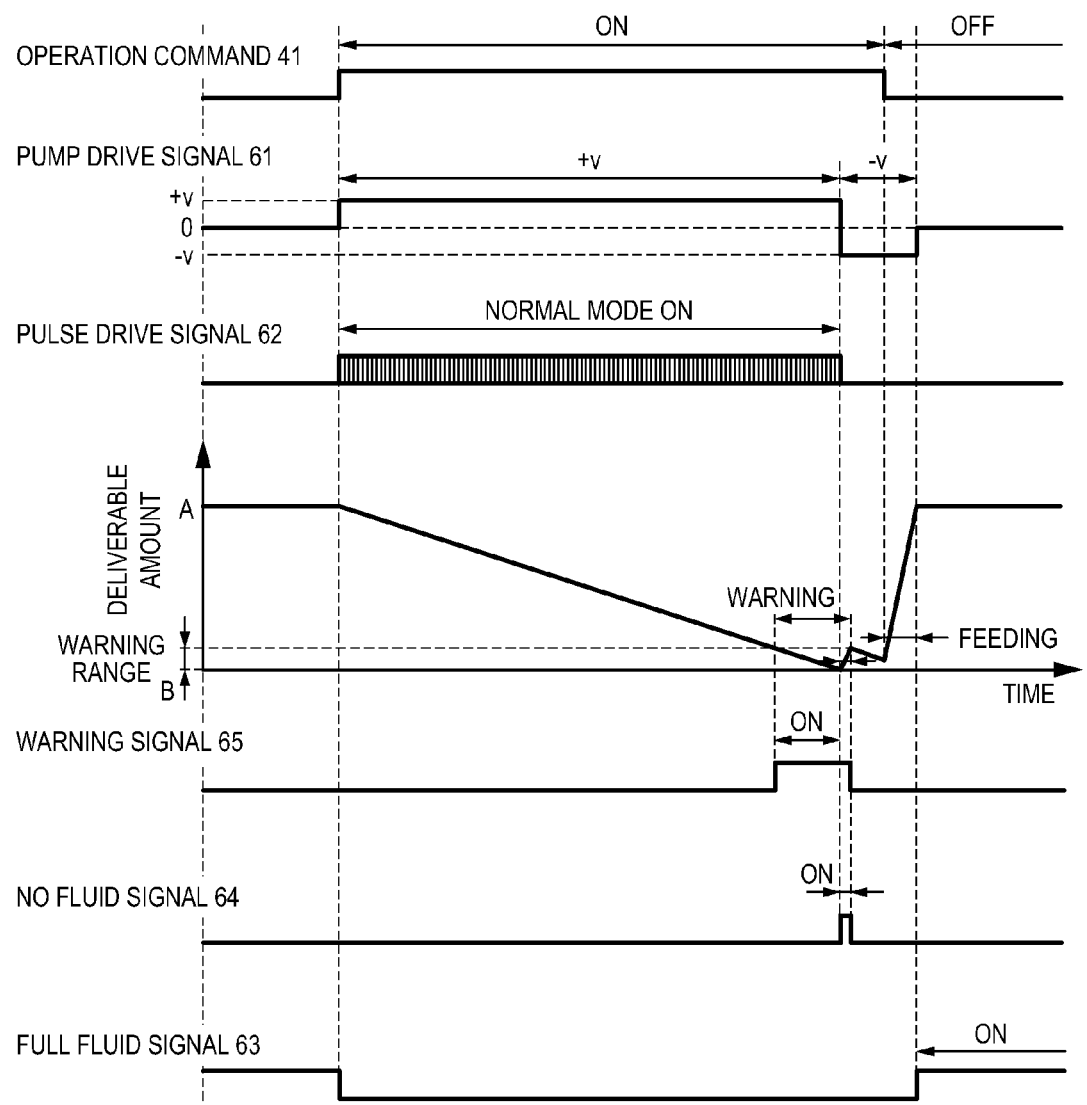
FIG. 7 is a timing diagram showing a fluid feeding operation of the fluid supply unit according to the present embodiment.

FIG. 7 is a timing diagram showing a fluid feeding operation of the fluid supply unit 10 according to the present embodiment. That is, FIG. 7 is a timing diagram showing the fluid feeding operation of the fluid supply unit 10 when ejection is continued for a long period of time, and the amount of deliverable fluid becomes zero. When the operator continuously outputs a command to the operation command input unit 40, and the operation command 41 is continuously in the ON state, the drive control unit 50 causes the pump drive signal 61 to be continuously in the forward rotation (+v) state, and the pulse drive signal 62 is continuously output.

When the pump drive signal 61 is continuously in the forward rotation (+v) state, the plunger 12 continues moving at a predetermined speed in a direction from the maximum volume level A to the minimum volume level B and finally reaches the minimum volume level B. The fluid is continuously delivered to the pulse generation unit 30, and finally the amount of deliverable fluid becomes zero, and the delivery stops. Operations in the vicinity of the minimum volume level B will be described below.

Warning

The random level detection sensor 27 (see FIG. 2) outputs the warning signal 65 (see FIG. 1) to the drive signal control unit 51 before the plunger 12 reaches the minimum volume level B. Upon receiving the warning signal 65, the drive signal control unit 51 outputs an alert (not shown) of no fluid to the operator. In this case, when the operator stops outputting a command in response to the alert, ejection stops and feeding starts as described above.

When the operator continues outputting a command rather than stopping it, the plunger 12 reaches the minimum volume level B.

Feeding

The first volume level detection sensor 26 detects arrival of the plunger 12 at the minimum volume level B and outputs the no fluid signal 64 to the drive signal control unit 51. Upon receiving the no fluid signal 64, the drive signal control unit 51 changes the pump drive signal 61 to the reverse rotation (-v) state and stops outputting the pulse drive signal 62. When the pump drive signal 61 is in the reverse rotation (-v) state, the plunger 12 starts moving in the direction toward the maximum volume level A, and the fluid supply unit 10 starts feeding fluid. Finally, the plunger 12 reaches the maximum volume level A. The second volume level detection sensor 25 detects arrival of the plunger 12 at the maximum volume level A and outputs the full fluid signal 63 to the drive signal control unit 51. Upon receiving the full fluid signal 63, the drive signal control unit 51 changes the pump drive signal 61 to the no rotation (0) state, and the plunger 12 stops its movement. Moreover, when the output of the pulse drive signal 62 stops, the pulse generation unit 30 stops generating pulses.

As above, when the operator continues outputting a command rather than stopping it so that the plunger 12 reaches the minimum volume level B, the pump drive signal 61 maintains the level of the reverse rotation (-v), and feeding is continued even if the operation command 41 is continuously in the ON state. However, when the operator stops outputting a command to change the operation command 41 to the OFF state and then outputs a command to change the operation command 41 to the ON state, the feeding mode is reset, and the pump drive signal 61 is changed to the level of the forward rotation (+v), and delivery of fluid restarts.

The position where the warning signal 65 is output can be adjusted by arbitrarily changing the position of the random level detection sensor 27. The period elapsed from the point in time when the operator continuously outputs a command to the operation command input unit 40, and the warning signal 65 starts being output to the point in time when the first volume level detection sensor 26 outputs the no fluid signal 64 may be checked in advance, and the position of the random level detection sensor 27 maybe adjusted appropriately in accordance with the using method of the operator.

As described above, according to the fluid ejection device 100 of the present embodiment, the following advantages can be obtained.

Since the supply of fluid to the pulse generation unit 30 and the generation of pulses in the fluid by the pulse generation unit 30 and ejection of the fluid are controlled by the drive signal control unit 51 in conjunction with the operation command 41, it is possible to start generation of pulsating flow in conjunction with ejection of fluid. Moreover, it is possible to stop ejection of fluid in conjunction with stopping of generation of pulsating flow. When performing surgery with ejection of pulsating flow as in the case of a water jet knife, since the surgery is performed while observing the state of an operation site, ejection of pulsating flow is often stopped during the surgery. When a treatment such as excision or incision is halted, ejection of fluid as well as generation of pulsating flow may often be stopped. Thus, it is possible to limit the amount of ejected fluid to an amount as small as necessary by interlocking the pump drive signal 61 with the pulse drive signal 62. In this way, even when a small amount of fluid is secured in the fluid supply unit 10, a sufficient amount of fluid is ejected, and surgery can be performed.

Moreover, the operation of feeding fluid into the pump chamber 11 starts when fluid is not ejected, and fluid is supplied into the pump chamber 11 whenever ejection stops, fluid is always secured in the pump chamber 11, and the operator can continue operations without paying any particular attention. As a result, even when a small amount of fluid is secured in the pump chamber 11, a sufficient amount of fluid is ejected, and surgery can be performed.

Furthermore, since the speed of feeding fluid into the pump chamber 11 is faster than the speed of delivering fluid from the pump chamber 11, fluid is supplied into the pump chamber 11 at a high speed when fluid is not ejected. Thus, since fluid is supplied into the pump chamber 11 at a high speed whenever ejection stops, fluid is always secured in the pump chamber 11, and the operator can continue operations without paying any particular attention. As a result, even when a small amount of fluid is secured in the pump chamber 11, a sufficient amount of fluid is ejected, and surgery can be performed.

Furthermore, since a sufficient amount of fluid is ejected even when a small amount of fluid is secured in the cylinder, and surgery can be performed, it is possible to configure the fluid ejection device with a compact single plunger fluid supply unit of which the structure and control can be simplified. As a result, it is possible to provide a fluid ejection device in which it is possible to secure high reliability of the pump, simplify the maintenance, and decrease manufacturing costs.

The invention is not limited to the above embodiment, and various changes and improvements can be made to the above embodiment. Modified examples will be described below. The same constituent elements as those of the first embodiment will be denoted by the same reference numerals, and redundant description thereof will not be provided.

MODIFIED EXAMPLE

An example in which a standby period where the output of a drive signal is stopped is set in order to obtain stable ejection of pulsating flow will be described. In this example, the pulse generation unit 30 starts generating pulses after the fluid supply unit 10 delivers fluid to the pulse generation unit 30, and delivery of fluid is stopped after the pulses are stopped. In this way, stable ejection of pulsating flow is obtained.

Figure 8:
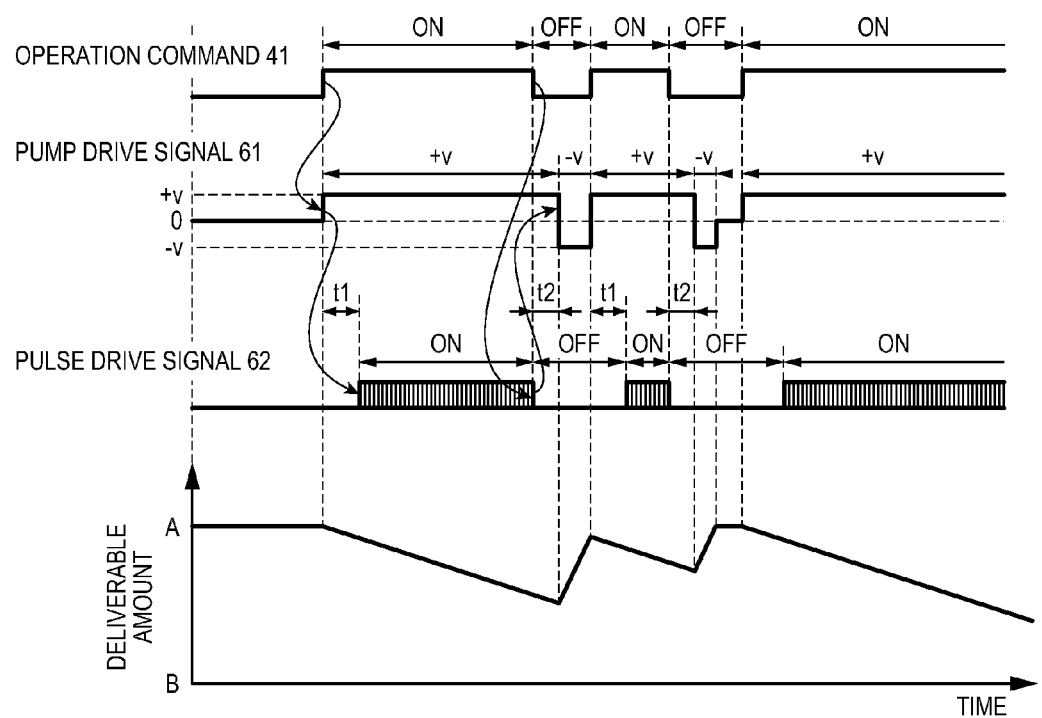
FIG. 8 is a timing diagram showing the relationship of standby periods of respective units according to a modified example.

FIG. 8 is a timing diagram showing the relationship of standby periods of respective units according to the modified example. The drive signal control unit 51 outputs the pulse drive signal 62 after a first standby period t1 elapses after the pump drive signal 61 is output. Moreover, the output of the pump drive signal 61 is stopped after a second standby period t2 elapses after the output of the pulse drive signal 62 is stopped.

By doing so, since the pulse drive signal 62 is output in a state where fluid is filled into a path extending from the fluid chamber 31 to the nozzle 71, it is possible to prevent the volume changing section 32 from be driven uselessly in a state where an insufficient amount of fluid is filled in the fluid chamber 31. Thus, since pulsating flow can be generated in a state where fluid is stably ejected when fluid ejection is repeatedly started and stopped, an amount of fluid sufficient for generating pulsating flow is secured in the pump chamber. Thus, blank ejection without fluid can be prevented. Moreover, when pulsating flow is generated after fluid is stably supplied up to the fluid ejection tube, since bubbles rarely enter into the fluid ejection device, ejection can be performed stably.

Medical Device

The fluid ejection device 100 described above can be used as a medical device, for example, a surgical tool for ejecting liquid such as physiological saline and a medicinal solution ejection apparatus for ejecting medicinal solution. By using the fluid ejection device 100 according to the invention as a medical device, even when a small amount of fluid is secured in the fluid supply unit 10, a sufficient amount of fluid is ejected, and the size of the pump chamber 11 can be decreased. Thus, the fluid ejection device 100 can be provided as a portable medical device for emergency use, and can be installed in a limited space.

As a specific use example, a case where the inner diameter of a cylinder is 25 mm, the stroke of a plunger is 200 mm, and the maximum continuous delivery amount is 98 ml will be described. When the amount of ejected fluid is 20 ml per minute, the maximum continuous fluid ejection period is about 5 minutes. Moreover, the time required for feeding 100 ml of fluid is about 3 seconds. That is, it is possible to realize a fluid ejection device capable of ejecting fluid continuously for several minutes by providing several seconds of interval.

Moreover, when the maximum fluid ejection pressure is 20 Atm, the drive force of the plunger is about 100 kgf.

As above, according to the fluid ejection device 100 of the present embodiment, it is possible to configure a fluid ejection device with a compact single plunger pump.

In the above-described embodiment, although a piezoelectric element is used as the volume changing section, the volume changing section is not limited to this. For example, vapor bubbles may be generated using an optical fiber. Moreover, vapor bubbles may be generated using discharge from an electrode. Furthermore, vapor bubbles may be generated using a heater.

This application claims priority to Japanese Patent Application No. 2010-287188, filed on Dec. 24, 2010, and No. 2011-166462, filed on July 29 the entirety of which is hereby incorporated by reference.

What is claimed is:

1. A fluid ejection device comprising:
a pulse generation unit that changes the volume of a fluid chamber using a volume changing section to eject pulsating flow;
a fluid supply unit including a pump chamber and a pump chamber volume changing section that cycles the volume of the pump chamber between a first volume and a second volume to supply the fluid to the pulse generation unit;
a drive control unit that inputs a pulsating flow drive signal for driving the pulse generation unit and inputs a fluid supply drive signal for driving the fluid supply unit; and
an operation command input unit that inputs an operation command to the drive control unit,
wherein the fluid supply drive signal and the pulsating flow drive signal are input in conjunction with the input of the operation command,
wherein the drive control unit is configured to drive the pump chamber volume changing section using the fluid supply drive signal such that:
the pump chamber volume changing section decreases the volume of the pump chamber toward the first volume until the volume of the pump chamber reaches the first volume when the operation command is input,
the pump chamber volume changing section increases the volume of the pump chamber towards the second volume when the volume of the pump chamber has reached the first volume and the operation command is input, and
the pump chamber volume changing section increases the volume of the pump chamber towards the second volume when the operation command is not input.

2. The fluid ejection device according to claim 1,
wherein the rate of increase of the volume of the pump chamber in which the fluid is fed into the pump chamber is faster than the rate of decrease of the volume of the pump chamber in which the fluid is delivered from the pump chamber.

3. The fluid ejection device according to claim 1,
wherein the drive control unit inputs the pulsating flow drive signal after a first period elapses after the fluid supply drive signal is input and stops inputting the fluid supply drive signal after a second period elapses after the input of the pulsating flow drive signal stops.

4. The fluid ejection device according to claim 1,
wherein the fluid supply unit includes
a second volume level detection sensor that detects arrival of the volume of the fluid stored in the pump chamber at the second volume level,
a first volume level detection sensor that detects arrival of the volume at the first volume level, and
a random level detection sensor that detects arrival of the volume at an arbitrary position between the first volume level and the second volume level.

5. The fluid ejection device according to claim 1,
wherein the first volume level is a value where the volume of the pump chamber reaches its minimum, and
wherein the second volume level is a value where the volume of the pump chamber reaches its maximum.

6. The fluid ejection device according to claim 1,
wherein the pump chamber includes a plunger and a cylinder in which the plunger is inserted, and
wherein the pump chamber volume changing section is a plunger driving section that moves the plunger within the cylinder.

7. The fluid ejection device according to claim 1,
wherein the operation command input unit is a switch, a foot switch, or a voice recognition device.

8. A medical device which uses the fluid ejection device according to claim 1.

9. A medical device which uses the fluid ejection device according to claim 2.

10. A medical device which uses the fluid ejection device according to claim 3.

11. A medical device which uses the fluid ejection device according to claim 4.

12. A medical device which uses the fluid ejection device according to claim 5.

13. A medical device which uses the fluid ejection device according to claim 6.

14. A medical device which uses the fluid ejection device according to claim 7.

* * * * *